US009546964B2

(12) United States Patent
Li et al.

(10) Patent No.: US 9,546,964 B2
(45) Date of Patent: Jan. 17, 2017

(54) DEFECT DETECTION SYSTEM FOR EXTREME ULTRAVIOLET LITHOGRAPHY MASK

(75) Inventors: Hailiang Li, Beijing (CN); Changqing Xie, Beijing (CN); Ming Liu, Beijing (CN); Dongmei Li, Beijing (CN); Jiebin Niu, Beijing (CN); Lina Shi, Beijing (CN); Xiaoli Zhu, Beijing (CN)

(73) Assignee: THE INSTITUTE OF MICROELECTRONICS OF CHINESE ACADEMY OF SCIENCES, Beijing (CN)

( * ) Notice: Subject to any disclaimer, the term of this patent is extended or adjusted under 35 U.S.C. 154(b) by 287 days.

(21) Appl. No.: 14/391,682

(22) PCT Filed: Apr. 16, 2012

(86) PCT No.: PCT/CN2012/074095
§ 371 (c)(1),
(2), (4) Date: Oct. 9, 2014

(87) PCT Pub. No.: WO2013/152516
PCT Pub. Date: Oct. 17, 2013

(65) Prior Publication Data
US 2015/0104094 A1    Apr. 16, 2015

(30) Foreign Application Priority Data
Apr. 10, 2012 (CN) .......................... 2012 1 0104156

(51) Int. Cl.
*G06K 9/00* (2006.01)
*G01N 21/88* (2006.01)
(Continued)

(52) U.S. Cl.
CPC .......... *G01N 21/8851* (2013.01); *G01N 21/47* (2013.01); *G01N 21/8806* (2013.01);
(Continued)

(58) Field of Classification Search
None
See application file for complete search history.

(56) References Cited

U.S. PATENT DOCUMENTS

| 7,368,744 B2 * | 5/2008 | Mulkens | G03F 7/70091 250/365 |
| 8,841,047 B2 * | 9/2014 | Yu | G03F 1/24 430/311 |
| 2012/0081684 A1 * | 4/2012 | Den Oef | G01N 21/94 355/67 |

FOREIGN PATENT DOCUMENTS

| CN | 101183210 | 5/2008 |
| CN | 101470270 | 7/2009 |

(Continued)

OTHER PUBLICATIONS

Juschkin et al., "EUV dark-field microscopy for defect inspection", 10th International Conference on X-Ray Microscopy 2010.*
(Continued)

*Primary Examiner* — Soo Jin Park
(74) *Attorney, Agent, or Firm* — Hogan Lovells US LLP

(57) ABSTRACT

A defect detection system for an extreme ultraviolet lithography mask comprises an extreme ultraviolet light source (1), extreme ultraviolet light transmission parts (2, 3), an extreme ultraviolet lithography mask (4), a photon sieve (6) and a collection (7) and analysis (8) system. Point light source beams emitted by the extreme ultraviolet light source (1) are focused on the extreme ultraviolet lithography mask (4) through the extreme ultraviolet light transmission parts (2, 3); the extreme ultraviolet lithography mask (4) emits scattered light and illuminates the photon sieve (6); and the photon sieve (6) forms a dark field image and transmits the same to the collection (7) and analysis (8) system. The defect detection system for the extreme ultraviolet photolithographic mask uses the photon sieve to replace a
(Continued)

Schwarzchild objective, thereby realizing lower cost, relatively small size and high resolution.

9 Claims, 7 Drawing Sheets

(51) Int. Cl.
| | | |
|---|---|---|
| *G03F 1/84* | (2012.01) | |
| *G02B 21/16* | (2006.01) | |
| *G02B 27/42* | (2006.01) | |
| *G01N 21/47* | (2006.01) | |
| *G01N 21/95* | (2006.01) | |
| *G06T 7/00* | (2006.01) | |
| *G01N 21/956* | (2006.01) | |

(52) U.S. Cl.
CPC ............. *G01N 21/95* (2013.01); *G02B 21/16* (2013.01); *G02B 27/4222* (2013.01); *G03F 1/84* (2013.01); *G06T 7/0004* (2013.01); *G01N 2021/8822* (2013.01); *G01N 2021/95676* (2013.01); *G01N 2201/12* (2013.01); *G02B 2207/125* (2013.01)

(56) References Cited

FOREIGN PATENT DOCUMENTS

| | | |
|---|---|---|
| CN | 101561637 | 10/2009 |
| CN | 101995408 | 3/2011 |
| CN | 103365073 | 10/2013 |
| WO | 2011015412 | 2/2011 |
| WO | 2013152516 | 10/2013 |

OTHER PUBLICATIONS

"International Search Report dated Jan. 17, 2013," International Application No. PCT/CN2012/074095, 6 pages.

* cited by examiner

DEFECT DETECTION SYSTEM FOR EXTREME ULTRAVIOLET LITHOGRAPHY MASK

RELATED APPLICATIONS

This application is a United States National Stage Application filed under 35 U.S.C 371 of PCT Patent Application Serial No. PCT/CN2012/074095, filed Apr. 16, 2012, which claims Chinese Patent Application Serial No. CN201210104156.5, filed Apr. 10, 2012, the disclosure of all of which are hereby incorporated by reference in their entirety.

TECHNICAL FIELD

The present application relates to the technical field of lithography of integrated circuits in semiconductor science, and in particular to a defect detection system for an extreme ultraviolet lithography mask.

BACKGROUND OF THE INVENTION

Since the 1970s, the graphic size in an integrated circuit has been continuously reduced in the semiconductor industry according to Moore's law, thereby increasing the number of transistors on a central processing unit (CPU) of a computer at the rate of doubling every two years. As the next generation of advanced lithography technology, 22 nm node-oriented extreme ultraviolet lithography opens up a new way with faster speed, smaller size and lower price for the semiconductor industry. However, through the difficult advancement of the EUV (extreme ultraviolet) lithography technology, we can appreciate that the development of the lithography technology is not only based on lithography machines, and the EUV can be just put into mass production as soon as possible through mutual coordination and optimization of other links, for example, appropriate photoresists, defect-free masks and the like are needed. At present, one of main bottlenecks in the development of the extreme ultraviolet lithography is lack of an imaging and detection technology for the masks to ensure the defect-free requirements of the extreme ultraviolet lithography masks.

As any substance has absorption limitation against working wavelength (13.5 nm), if transmission exposure is adopted, the mask can absorb EUV light and the light intensity is greatly reduced. Therefore, in comparison with an existing projection type optical system, the EUV mask adopts a reflection technology rather than a transmission technology. Generally, the manufacturing of the EUV mask adopts a multi-layer stacked Mo/Si film, each of Mo layers and Si layers must be smooth enough and the error allowable range is the size of only one atom. Even dust particles with the size of 10 nm fall on the surface of the mask, serious defects on all samples formed by lithography may be caused. On the standard six-inch (152.4 mm×152.4 mm) mask, such small defects may damage the whole mask and the lithography results. It becomes a crux how to obtain a defect-free multi-layer anti-reflection film on the surface of the mask. Furthermore, very small bulges or depressions on a substrate may also cause the changes in reflection light phase after being covered by the multi-layer film. Such phase type defects may only be about 1 nm in size, so that the phase type defects are almost impossible to be detected by other detection methods in addition to an actual at-wavelength inspection technology. The defects of the extreme ultraviolet lithography mask may appear to have great differences under different detection light sources; if the defects are amplitude type defects, the defects are very small and the wavelength of the required detection light source needs to be smaller than the defects; and if the defects are the phase type defects, in the actual application, the defects in such type are only sensitive to extreme ultraviolet wave bands. Therefore, researchers need to design a special detection system to detect the different types of mask defects. At present, on the road of extreme ultraviolet lithography commercialization, a high-speed and high-resolution mask defect detection and imaging system is essential to ensure the defect-free masks.

However, most of imaging lens used by a currently developed extreme ultraviolet lithography mask detection system use a Schwarzchild objective, which has great processing difficulty, high cost and large volume, so that the difficulty of implementation of the extreme ultraviolet lithography mask detection system is increased.

SUMMARY OF THE INVENTION

The technical problem to be solved in the application is to provide a defect detection system for an extreme ultraviolet lithography mask, which has the advantages of lower cost, relatively smaller size and high resolution.

In order to solve the above technical problem, the defect detection system for the extreme ultraviolet lithography mask provided in the application comprises an extreme ultraviolet light source, extreme ultraviolet light transmission parts for transmitting light signals, an extreme ultraviolet lithography mask, a photon sieve and a collection and analysis part which is used for collecting a dark field image and determining the type of defects and the positions of the defects; point light source beams emitted by the extreme ultraviolet light source are focused on the extreme ultraviolet lithography mask through the extreme ultraviolet light transmission parts; the extreme ultraviolet lithography mask emits scattered light and illuminates the photon sieve; and the photon sieve forms the dark field image and transmits the same to the collection and analysis part.

Further, the extreme ultraviolet light transmission parts comprise a multi-layer film concave plane condenser and a multi-layer film plane reflector; and the point light source beams emitted by the extreme ultraviolet light source are focused on the extreme ultraviolet lithography mask after sequentially passing through the multi-layer film concave plane condenser and the multi-layer film plane reflector.

Further, the multi-layer film structure of each of the multi-layer film concave plane condenser and the multi-layer film plane reflector is a molybdenum/silicon multi-layer film, the period P is 6.938 nm, the thickness of each layer of molybdenum is 0.4 time the period P, the thickness of each layer of silicon is 0.6 time the period P and each molybdenum/silicon multi-layer film has 40 periods in total; the extreme ultraviolet light source is a point light source, the wavelength λ is 13.5 nm and the average power is 10 μw; and the photon sieve is distributed on a silicon nitride film window, the thickness of a silicon nitride film is 100 nm, the hole diameter of an outmost ring of the photon sieve is 40 nm and the focal length is 1 mm.

Further, the extreme ultraviolet lithography mask comprises a low thermal expansion substrate, a multi-layer film reflection layer and an absorption layer graph; the low thermal expansion substrate adopts microcrystalline glass material and has the dimension of 152.4 mm×152.4 mm×6.35 mm; the multi-layer film reflection layer is a molybdenum/silicon multi-layer film, the period P is 6.938 nm, the thickness of each layer of molybdenum is 0.4 time the period P, the thickness of each layer of silicon is 0.6 time the period P and the multi-layer film reflection layer has 40 periods in total; the absorption layer graph adopts chromium material and has the thickness of 70 nm; and the absorption layer graph is divided into three regions, an outer ring is an operation region, an intermediate ring is a marking region and an inner ring is a graph region.

Further, the defect detection system for the extreme ultraviolet lithography mask further comprises a vacuum cavity and a bearing part; the extreme ultraviolet lithography mask is arranged on the bearing part; and the multi-layer film concave plane condenser, the multi-layer film plane reflector, the photon sieve and the extreme ultraviolet lithography mask are respectively arranged in the vacuum cavity.

Further, the bearing part comprises a sample scanning table and a vibration isolation table; the sample scanning table is arranged on a bearing table; and the sample scanning table is arranged in the vacuum cavity.

Further, the working modes of the vibration isolation table comprise a passive vibration damping mode and an active vibration damping mode.

Further, the regulation range of the sample scanning table in the X-direction or Y-direction is greater than or equal to 140 mm×140 mm and the resolution is 2 μm; the minimum scanning stepping is less than or equal to 0.2 nm; and the sample scanning table can be performed regulation within the range of 0 to 20 mm in the Z-direction.

Further, the collection and analysis system comprises a collection device for collecting the dark field image from the photon sieve and an analysis device; and the collection device is connected with the analysis device.

Further, the collection device is a CCD camera or an X-ray CCD camera; and the working mode of the CCD camera or the X-ray CCD camera is a back lighting mode.

The defect detection system for the extreme ultraviolet lithography mask provided in the application utilizes the properties that the photon sieve has small size, is easy to be processed, and has low cost and high resolution to replace a Schwarzchild objective with great processing difficulty, high cost and large size; and the defect detection system for the extreme ultraviolet lithography mask has the characteristics of lower cost, relatively small size and high resolution.

DETAILED DESCRIPTION OF PREFERRED EMBODIMENTS

Figure 1:
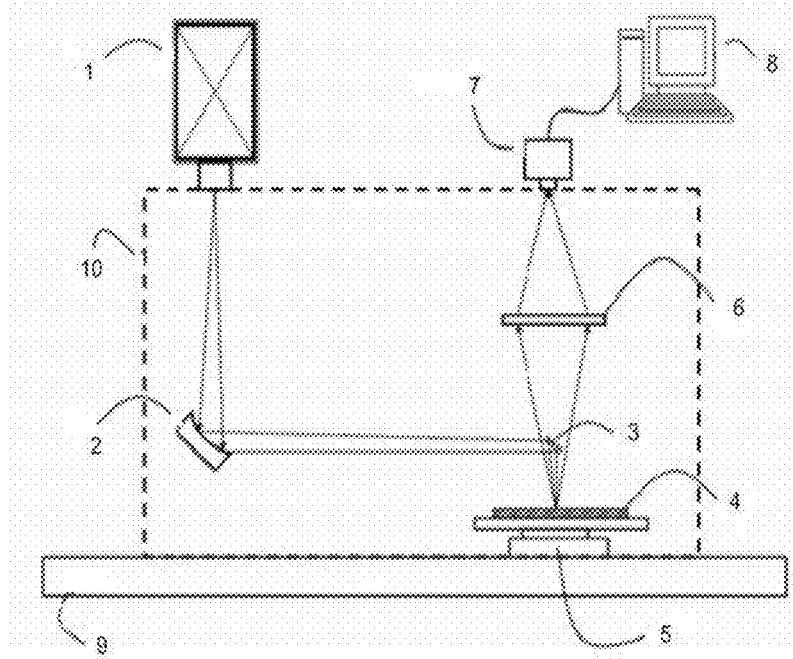
FIG. 1 is a structure diagram of a defect detection system for an extreme ultraviolet lithography mask in the preferred embodiment of the present application.

Referring to FIG. 1, a defect detection system for an extreme ultraviolet lithography mask in the preferred embodiment of the present invention comprises an extreme ultraviolet light source 1, extreme ultraviolet light transmission parts for transmitting light signals, an extreme ultraviolet lithography mask 4, a photon sieve 6 and a collection and analysis part which is used for collecting a dark field image and determining the type of defects and the positions of the defects, wherein the extreme ultraviolet light transmission parts comprise a multi-layer film concave plane condenser 2 and a multi-layer film plane reflector 3; and the point light source beams emitted by the extreme ultraviolet light source 1 are focused on the extreme ultraviolet lithography mask 4 after sequentially passing through the multi-layer film concave plane condenser 2 and the multi-layer film plane reflector 3. The collection and analysis part comprises a collection device 7 and an analysis device 8 for determining the type of defects and the positions of the defects (which can be achieved by a PC). The extreme ultraviolet lithography mask 4 emits scattered light and illuminates the photon sieve 6; and the photon sieve 6 forms the dark field image and transmits the same to the collection device 7. The collection device 7 is a CCD camera or an X-ray CCD camera; and the CCD camera or the X-ray CCD camera works in a back lighting mode.

The defect detection system for the extreme ultraviolet lithography mask in the preferred embodiment of the present application further comprises a vacuum cavity 10, a sample scanning table 5 and a vibration isolation table 9. The extreme ultraviolet lithography mask 4 is arranged on the sample scanning table 5. The sample scanning table 5 is arranged on the vibration isolation table 9. The concave plane condenser 2, the multi-layer film plane reflector 3, the photon sieve 6, the extreme ultraviolet lithography mask 4 and the sample scanning table 5 are respectively arranged in the vacuum cavity 10. The vibration isolation table 9 bears the whole mask detection system and has a passive vibration damping mode and an active vibration damping mode.

The extreme ultraviolet light source 1 is a point light source, the wavelength λ of extreme ultraviolet light is about 13.5 nm ($\Delta\lambda/\lambda<1\times10^{-4}$) and the average power is 10 μw.

Figure 2:
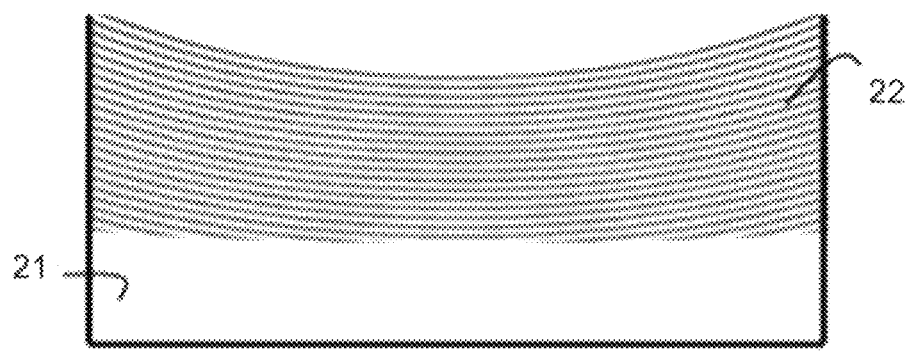
FIG. 2 is a structure diagram of a concave plane condenser in the preferred embodiment of the present application.

Referring to FIG. 2, the multi-layer film concave plane condenser 2 comprises microcrystalline glass 21 and a molybdenum/silicon multi-layer film 22 (wherein molybdenum layers and silicon layers are distributed at intervals); and the period P of the molybdenum/silicon multi-layer film is 6.938 nm, the thickness of each layer of molybdenum is 0.4 time the period P, the thickness of each layer of silicon is 0.6 time the period P and the molybdenum/silicon multi-layer film has 40 periods in total.

Figure 3:
FIG. 3 is a structure diagram of a plane reflector in the preferred embodiment of the present application.

Referring to FIG. 3, the multi-layer film plane reflector 3 comprises the microcrystalline glass 31 and the molybdenum/silicon multi-layer film 32 (wherein molybdenum layers and silicon layers are distributed at intervals); and the period P (the sum of the thickness of one layer of molybdenum and the thickness of one layer of silicon is taken as one period) of the molybdenum/silicon multi-layer film is 6.938 nm, the thickness of each layer of molybdenum is 0.4 time the period P, the thickness of each layer of silicon is 0.6 time the period P and the molybdenum/silicon multi-layer film has 40 periods in total.

Figure 4:
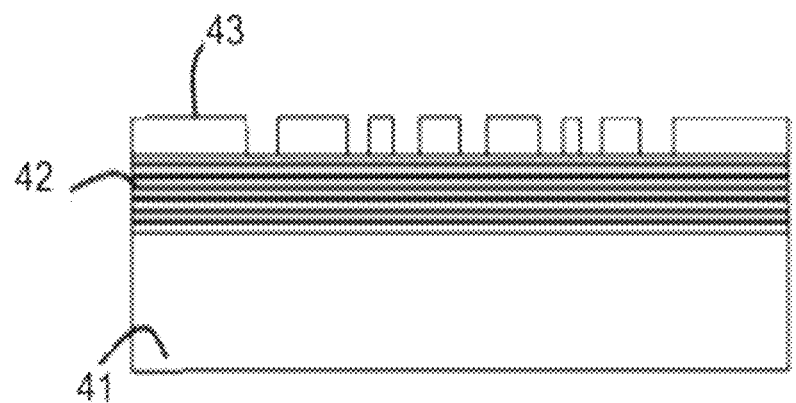
FIG. 4 is a structure diagram of the extreme ultraviolet lithography mask in the preferred embodiment of the present application.
Figure 5:
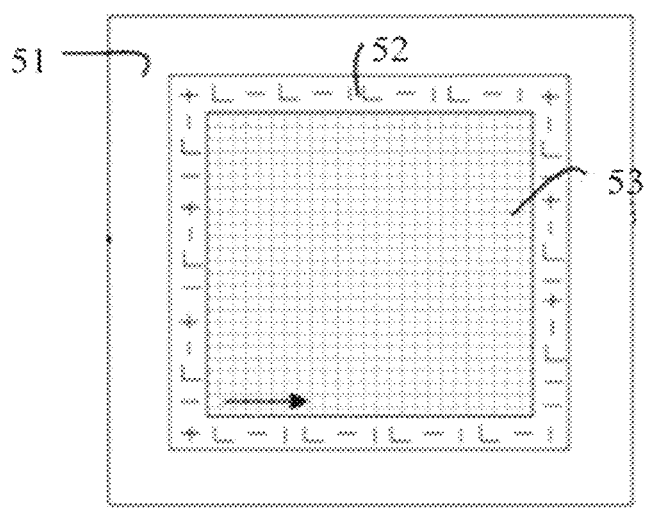
FIG. 5 is a top view of an absorption layer of the extreme ultraviolet lithography mask in the preferred embodiment of the present application.

Referring to FIG. 4, the extreme ultraviolet lithography mask 4 comprises a low thermal expansion substrate 41, a multi-layer film reflection layer 42 and an absorption layer graph 43; the low thermal expansion substrate 41 adopts microcrystalline glass material and has the dimension of 152.4 mm×152.4 mm×6.35 mm; the multi-layer film reflection layer 42 is a molybdenum/silicon multi-layer film, the period P (the sum of the thickness of one layer of molybdenum and the thickness of one layer of silicon is taken as one period) is 6.938 nm, the thickness of each layer of molybdenum is 0.4 time the period P, the thickness of each layer of silicon is 0.6 time the period P and the multi-layer film reflection layer has 40 periods in total; and the absorption layer graph 43 adopts chromium material and has the thickness of 70 nm. Referring to FIG. 5, the absorption layer graph 43 is divided into three regions, an outermost ring is an operation region 51, an intermediate ring is a marking region 52 and an innermost ring is a graph region 53.

The regulation range of the sample scanning table 5 in the X-direction or Y-direction is greater than or equal to 140 mm×140 mm and the resolution is 2 μm; the minimum scanning stepping is less than or equal to 0.2 nm; and the sample scanning table can be performed regulation within the range of 0 to 10 mm in the Z-direction.

Figure 6:
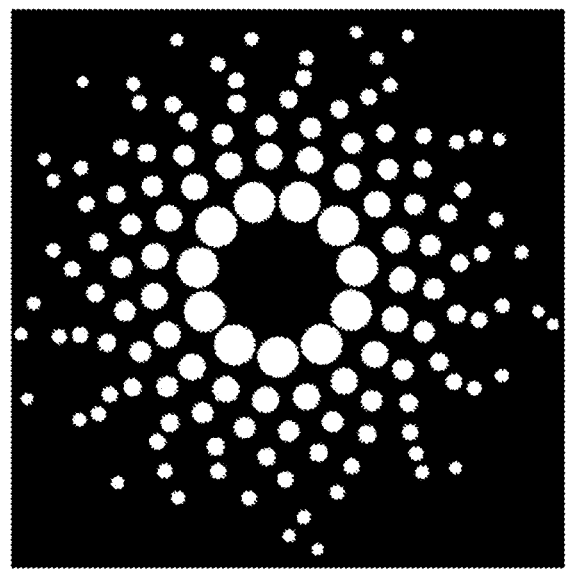
FIG. 6 is a schematic diagram of a photon sieve in the preferred embodiment of the present application.

Referring to FIG. 6, the photon sieve 6 is distributed on a silicon nitride film window, the thickness of a silicon nitride film is 100 nm, the hole diameter of the outmost ring of the photon sieve 6 is 40 nm and the focal length is 1 mm.

Figure 7:
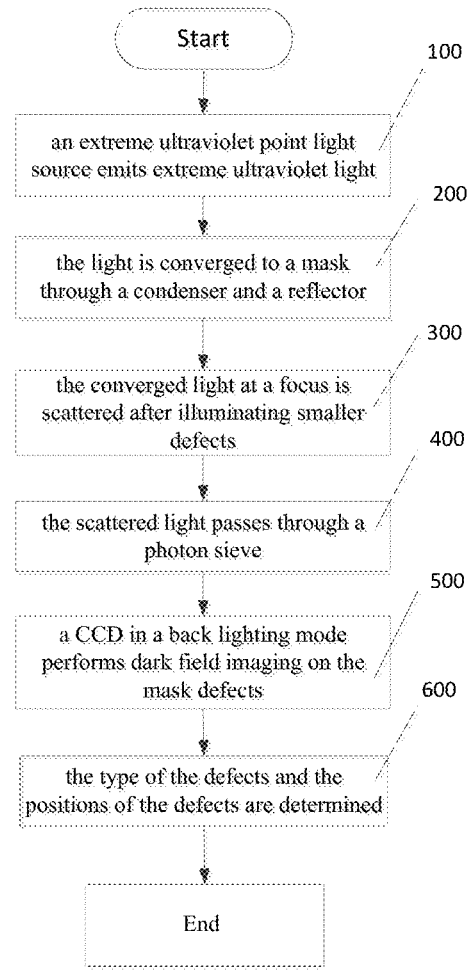
FIG. 7 is a work flow diagram of the defect detection system for the extreme ultraviolet lithography mask in the preferred embodiment of the present application.

Then, the work flow of a defect detection system for an extreme ultraviolet lithography mask in the preferred embodiment of the present invention is described in detail in combination with FIG. 7, and the work flow mainly comprises the following steps:

Step 100: an extreme ultraviolet point light source 1 emits extreme ultraviolet light after being excited.

Step 200: the extreme ultraviolet light is converged on an extreme ultraviolet lithography mask 4 through a multi-layer film concave plane condenser 2 and a multi-layer film plane reflector 3.

Step 300: when focused beams illuminate defects on the mask 4, scattered light is emitted and the multi-layer film plane reflector 3 covers a large area of the reflected light.

Step 400: the scattered light carries graphic information of the defects and illuminates a photon sieve 6.

Step 500: the photon sieve 6 then performs dark field imaging and a CCD camera 7 in a back lighting mode converts a formed dark field image to digital information.

Step 600: the digital information is conveyed to an analysis device 8 (such as a PC) used to determine the type of the defects and the positions of the defects; and then a sample scanning table readjusts the position of the mask for reimaging till the end of detection of a graph of the whole mask.

The defect detection system for the extreme ultraviolet lithography mask in the preferred embodiment of the present invention has the following beneficial effects: the properties of small size, easy processing, low cost and high resolution of the photon sieve are utilized to replace a Schwarzchild objective with great processing difficulty, high cost and large size; and the defect detection system for the extreme ultraviolet lithography mask with lower cost, relatively small size and high resolution is further realized.

Finally, it should be noted that the above specific implementations are only used for describing rather than limiting the technical solutions of the invention. Although the invention is described in detail by referring to the embodiments, those of ordinary skill in the art should understand that modifications or equivalent substitutions can be made to the technical solutions of the invention without deviating from the spirit and the scope of the technical solutions of the invention and should be included in the scope of the claims of the invention.

The invention claimed is:

1. A defect detection system for an extreme ultraviolet lithography mask, comprising
   an extreme ultraviolet light source;
   a plurality of extreme ultraviolet light transmission components configured to transmit light signals;
   an extreme ultraviolet lithography mask;
   a photon sieve; and
   a collection and analysis component configured to collect a dark field image and determine types of defects and positions of the defects,
   wherein point light source beams emitted by the extreme ultraviolet light source are focused on the extreme ultraviolet lithography mask through the extreme ultraviolet light transmission components;
   wherein the extreme ultraviolet lithography mask is configured to emit scattered light and illuminate the photon sieve;
   wherein the photon sieve forms the dark field image and transmits the dark field image to the collection and analysis component and
   wherein the plurality of extreme ultraviolet light transmission components comprise:
   a multi-layer film concave plane condenser and a multi-layer film plane reflector, wherein the point light source beams emitted by the extreme ultraviolet light source are focused on the extreme ultraviolet lithography mask after sequentially passing through the multi-layer film concave plane condenser and the multi-layer film plane reflector.

2. The defect detection system for the extreme ultraviolet lithography mask of claim 1, wherein the multi-layer film structure of each of the multi-layer film concave plane condenser and the multi-layer film plane reflector is a molybdenum/silicon multi-layer film, the period P is 6.938 nm, the thickness of each layer of molybdenum is 0.4 time the period P, the thickness of each layer of silicon is 0.6 time the period P and each molybdenum/silicon multi-layer film has 40 periods in total; wherein the extreme ultraviolet light source is a point light source, the wavelength λ is 13.5 nm and the average power is 10 μw; and wherein the photon sieve is distributed on a silicon nitride film window, the thickness of a silicon nitride film is 100 nm, the hole diameter of an outmost ring of the photon sieve is 40 nm and the focal length is 1 mm.

3. The defect detection system for the extreme ultraviolet lithography mask of claim 1, wherein the extreme ultraviolet lithography mask comprises a low thermal expansion substrate, a multi-layer film reflection layer and an absorption layer graph; wherein the low thermal expansion substrate adopts microcrystalline glass material and has the dimension of 152.4 mm×152.4 mm×6.35 mm; the multi-layer film reflection layer is a molybdenum/silicon multi-layer film, the period P is 6.938 nm, the thickness of each layer of molybdenum is 0.4 time the period P, the thickness of each layer of silicon is 0.6 time the period P and the multi-layer film reflection layer has 40 periods in total; and wherein the absorption layer graph adopts the material of chromium and has the thickness of 70 nm; and wherein the absorption layer graph is divided into three regions including an outer ring that is an operation region, an intermediate ring that is a marking region, and an inner ring that is a graph region.

4. The defect detection system for the extreme ultraviolet lithography mask of claim 1, wherein further comprising:

a vacuum cavity and a bearing part, wherein the extreme ultraviolet lithography mask is arranged on the bearing part; and wherein the multi-layer film concave plane condenser, the multi-layer film plane reflector, the photon sieve and the extreme ultraviolet lithography mask are respectively arranged in the vacuum cavity.

5. The defect detection system for the extreme ultraviolet lithography mask of claim 4, wherein working modes of the vibration isolation table comprise a passive vibration damping mode and an active vibration damping mode.

6. The defect detection system for the extreme ultraviolet lithography mask of claim 4, wherein a regulation range of a sample scanning table in the X-direction or Y-direction is greater than or equal to 140 mm×140 mm and the resolution is 2 μm; the minimum scanning stepping is less than or equal to 0.2 nm; and the sample scanning table can be performed regulation within the range of 0 to 10 mm in the Z-direction.

7. The defect detection system for the extreme ultraviolet lithography mask of claim 1, wherein the bearing part comprises:

a sample scanning table and a vibration isolation table, wherein the sample scanning table is arranged on a bearing table; and wherein the sample scanning table is arranged in the vacuum cavity.

8. The defect detection system for the extreme ultraviolet lithography mask of claim 1, wherein the collection and analysis component comprises:

a collection device for collecting the dark field image from the photon sieve, and an analysis device connected with the analysis device.

9. The defect detection system for the extreme ultraviolet lithography mask of claim 8, wherein the collection device is a CCD camera or an X-ray CCD camera; and a working mode of the CCD camera or the X-ray CCD camera is a back lighting mode.

* * * * *